(12) United States Patent
Tateno

(10) Patent No.: US 6,665,112 B2
(45) Date of Patent: Dec. 16, 2003

(54) OPTICAL RETICLE SUBSTRATE INSPECTION APPARATUS AND BEAM SCANNING METHOD OF THE SAME

(75) Inventor: Motonari Tateno, Tokyo (JP)

(73) Assignee: NEC Corporation, Tokyo (JP)

(*) Notice: Subject to any disclaimer, the term of this patent is extended or adjusted under 35 U.S.C. 154(b) by 0 days.

(21) Appl. No.: 10/357,487

(22) Filed: Feb. 4, 2003

(65) Prior Publication Data

US 2003/0117683 A1 Jun. 26, 2003

Related U.S. Application Data

(62) Division of application No. 09/998,521, filed on Nov. 29, 2001, now Pat. No. 6,538,795.

(30) Foreign Application Priority Data

Nov. 30, 2000 (JP) ........................................ 2000-364551

(51) Int. Cl.[7] ................................................ G02F 1/33
(52) U.S. Cl. .......................... 359/305; 359/285; 359/311
(58) Field of Search ................................ 359/286, 287, 359/285, 305, 307, 312, 311, 314; 347/239, 135, 255; 348/754, 769; 372/13; 324/76, 37; 385/7

(56) References Cited

U.S. PATENT DOCUMENTS 5,224,860 A * 7/1993 Waldman et al. ............. 434/21
5,521,036 A * 5/1996 Iwamoto et al. ............. 430/22
5,572,598 A * 11/1996 Wihl et al. .................. 382/144
6,320,658 B1 * 11/2001 Mizutani ..................... 356/399

FOREIGN PATENT DOCUMENTS

JP 59-30521 2/1984
JP 2000-66374 3/2000

OTHER PUBLICATIONS

Copy of Japanese Office Action dated Apr. 15, 2003 (and English translation of relevant portion).
Abstract of Handbook of Optical Engineering (and English translation of relevant portion) Feb. 20, 1986, 515–516.

* cited by examiner

Primary Examiner—Jordan M. Schwartz
Assistant Examiner—Jessica Stultz
(74) Attorney, Agent, or Firm—Dickstein, Shapiro, Morin & Oshinsky, LLP.

(57) ABSTRACT

An optical reticle substrate inspection apparatus is provided with a laser, a first acoustooptical element which scans a laser beam output from the laser, an a second acoustooptical element which generates a virtual image with a concave lens effect to the laser beam output from the first acoustooptical element. The optical reticle substrate inspection apparatus is further provided with a concave lens arranged on the output side of the laser beam of the second acoustooptical element and an optical system which images the virtual image on a reticle substrate being an object to be inspected. The concave lens magnifies the laser beam in a perpendicular direction to the scanning direction by the first acoustooptical element.

4 Claims, 4 Drawing Sheets

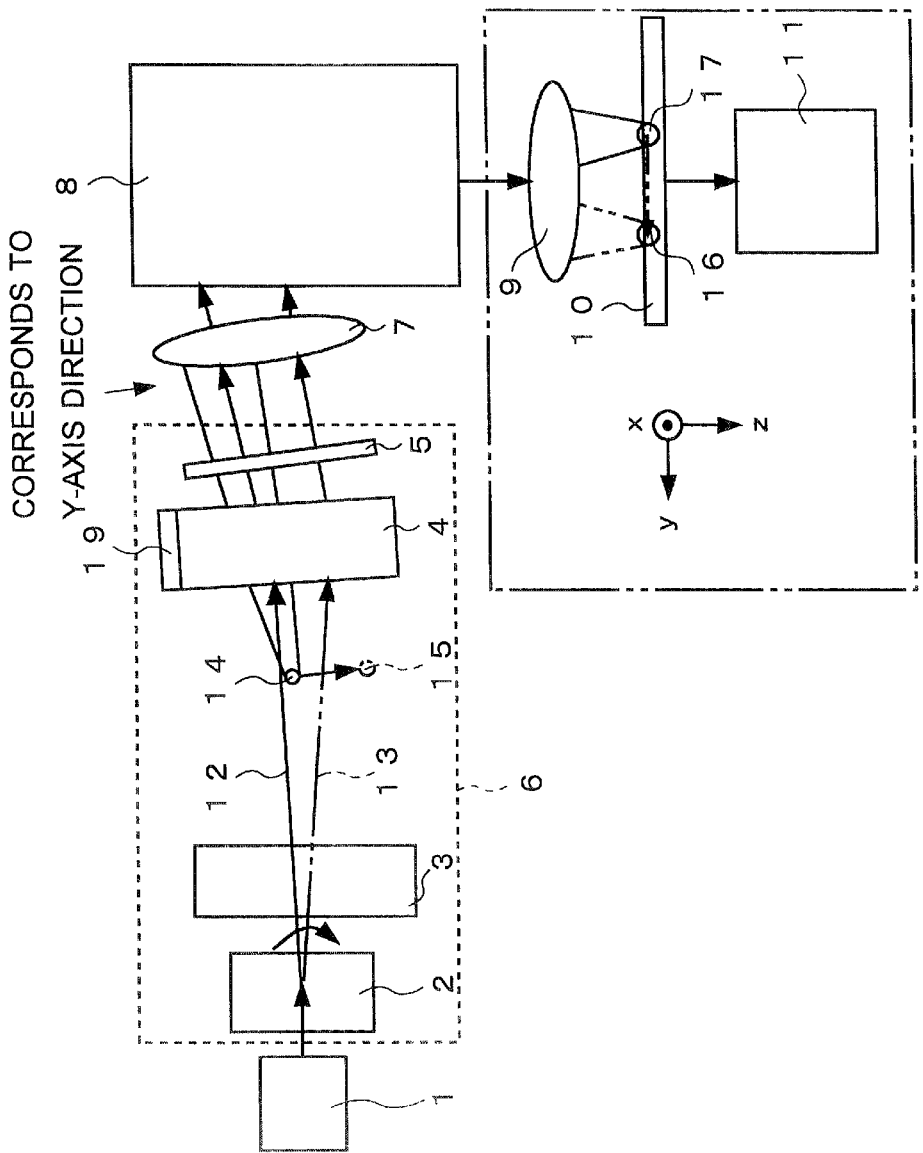

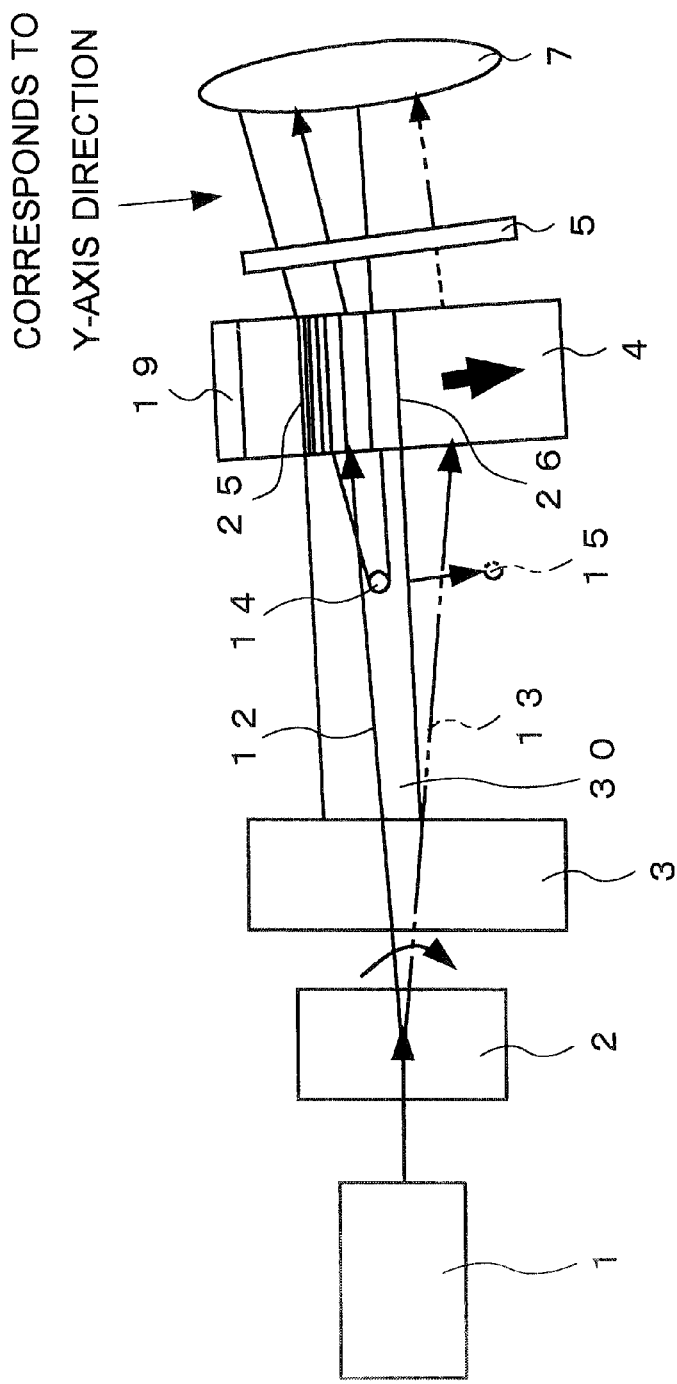

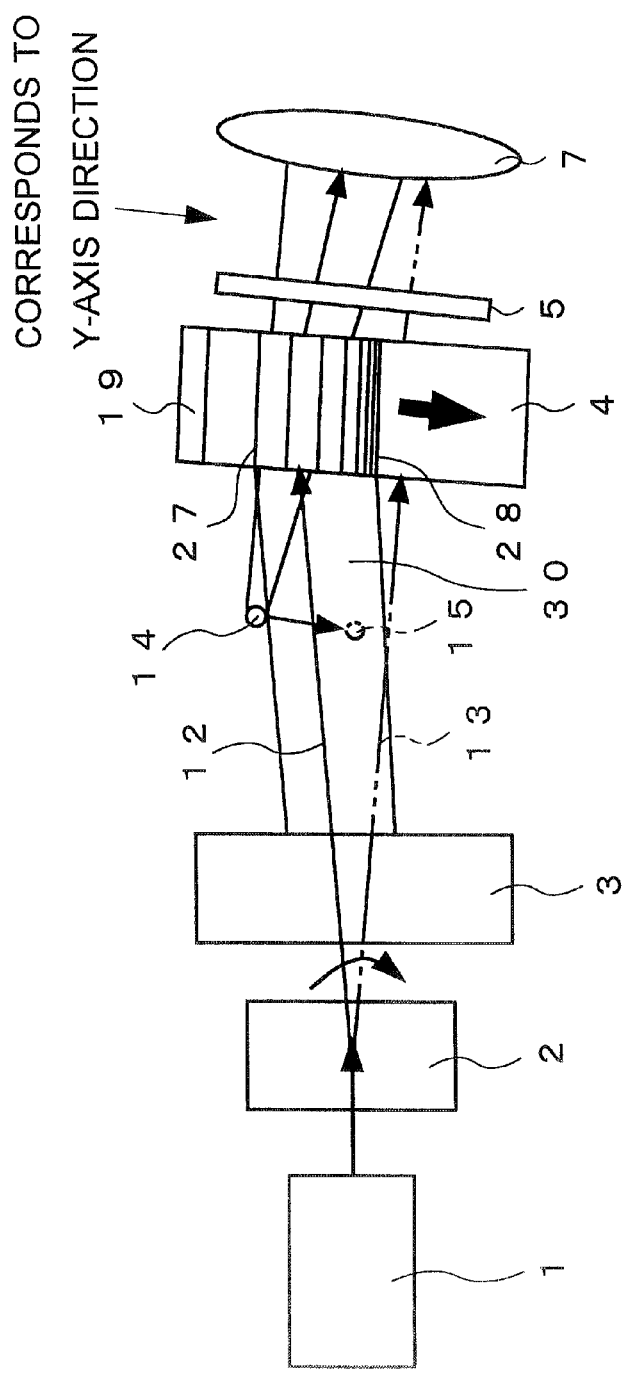

OPTICAL RETICLE SUBSTRATE INSPECTION APPARATUS AND BEAM SCANNING METHOD OF THE SAME

CROSS REFERENCE TO RELATED APPLICATIONS

This a divisional of U.S. patent application Ser. No. 09/998,521, filed Nov. 29, 2001, in the name of Motonari Tateno now U.S. Pat. No. 6,538,795.

BACKGROUND OF THE INVENTION

1. Field of the Invention

The present invention relates to an optical reticle substrate inspection apparatus that inspects a defect and a line width of a reticle substrate and a beam scanning method thereof, particularly, to an optical reticle substrate inspection apparatus for improving stability when a laser light source having a short wavelength is used and a beam scanning method thereof.

2. Description of the Related Art

In the optical reticle substrate inspection apparatus that inspects a defect and a line width of a reticle substrate, there exists an apparatus in which detection light is converged onto a substrate to detect the defect and the line width by transmission light or reflection light. In such a apparatus, a spot of a laser beam (a beam spot) is scanned in one direction parallel with a surface of the reticle substrate (hereinafter, this direction is referred to as a Y-axis direction), and a stage on which the reticle substrate is mounted is moved in an isokinetic manner in a direction parallel with the surface of the reticle substrate and a perpendicular direction to the Y-axis direction (hereinafter, this direction is referred to as an X-axis direction), and thus inspecting the defect and the like of the reticle substrate. As a scanning method of the beam spot, a method in which the beam spot is optically scanned is generally used in order to process inspection in a short time, and the beam scanning method using an acoustooptical element has been conventionally adopted.

In such a beam scanning method, aberration occurs to an angle of the scanning beam when the beam is converged by a normal cylindrical lens, and defocus occurs on the reticle substrate surface. For this reason, a method is adopted where the beam is converged using a lens effect by the acoustooptical element to reduce the defocus. A method converging the beam using the two acoustooptical elements is described in The U.S. Pat. No. 3,851,951, for example. And a substrate inspection apparatus that adopted the method is described in Japanese Patent Laid-Open (unexamined) No. Hei 6-294750. FIG. 1 is a schematic view showing the conventional optical reticle substrate inspection apparatus.

In the optical reticle substrate inspection apparatus, a laser light source 1, an acoustooptical element 2 and a group of cylindrical lenses 3 are arranged in this order in a rectilinear direction of a laser beam output from the laser light source 1. The acoustooptical element 2 is arranged so as to scan the laser beam output from the laser light source 1 in a perpendicular direction to the straight line by frequency modulation, and the group of cylindrical lenses 3 is arranged so as to magnify the laser beam output from the acoustooptical element 2 only in the scanning direction by the acoustooptical element 2.

An acoustooptical element 4a which gives a cylindrical lens effect to the laser beam output from the group of cylindrical lenses 3 is further provided to the optical reticle substrate inspection apparatus. A transducer 19 which oscillates ultrasonic to the acoustooptical element 4a is attached to one end portion of the acoustooptical element 4a. The acoustooptical element 4a is arranged such that a side where the transducer 19 is attached, that is, a side where the ultrasonic is input, is closer to the group of cylindrical lenses 3. Furthermore, a group of the cylindrical convex lenses 18 that converges the laser beam output from the acoustooptical element 4a is arranged in the optical reticle substrate inspection apparatus. Moreover, a relay lens 24 which propagates the laser beam passed through the convergence spot to an optical system (not shown) in a post-step is arranged on a position apart from the convergence spot formed by the group of cylindrical convex lenses 18. In addition, an objective lens (not shown) is arranged between the optical system and the reticle substrate being an object to be inspected, and a detector (not shown) that detects intensity and the like of the laser beam passed through the reticle substrate is further provided.

In the optical reticle substrate inspection apparatus constituted in this manner, scanning is performed in an angle made by an incident direction and an output direction to the laser beam output from the laser light source 1 by utilizing the frequency modulation by the first acoustooptical element 2. An optical path of the laser beam transits from a path 12 to a path 13 due to this process. When the laser beam has its optical path on the path 12, the laser beam is magnified by the group of cylindrical lenses 3 and output as a laser beam 30 with a width in the scanning direction.

Further, transducer 19 outputs a series of ultrasonic which is swept such that a wavelength lengthens in linear state as the passage of time, that is, the wavelength in a forefront portion 21 becomes shorter than that of an aftermost portion 20. A plurality of parallel lines between an aftermost portion 20 and a forefront portion 21 in FIG. 1 show that the wider the distance between the lines the longer the wavelength. The second acoustooptical element 4a, when the laser beam 30 is made incident thereto, outputs the laser beam 30 while converging it with functioning as a cylindrical convex lens by the ultrasonic oscillated from the transducer 19. The laser beam 30 output from the acoustooptical element 4a is further converged by the group of cylindrical convex lenses 18 to form a convergence spot 22. When the laser beam has its optical path on the path 13, a convergence spot 23 is formed on a position off from the convergence spot 22 in the scanning direction. The laser beam 30 passed through the convergence spot 22 is made incident to the relay lens 24 while magnifying its width again. Then, the convergence spot 22 is imaged on the reticle substrate via the optical system and the objective lens, and the detector detects the intensity and the like of the transmission light.

Note that the same detection can be performed even if the acoustooptical element 4a is arranged such that the side where the ultrasonic is input is made far from the group of cylindrical lenses 3 and the ultrasonic is swept such that the wavelength becomes shorter in linear state as the passage of time.

However, in recent years, although higher resolving power has been demanded for an apparatus for inspecting the reticle substrate with demand for finer pattern, there is a problem that the conventional optical reticle substrate inspection apparatus cannot provide sufficient high resolving power.

As a method of obtaining the high resolving power, a method is considered where the convergence spot size on the reticle substrate surface is made small by shortening the wavelength of the detection light. Progress of shorter wavelength has been made also in the field of exposure due to advancement in technology. It is important that the wavelength of the detection light is shortened to make it close to that of an exposure light because the way how the defect appears changes depending on a detection wavelength. However, in the case of shortening the wavelength of the detection light, a usable material of the acoustooptical element is limited due to a problem of material absorption regarding the scanning method where convergence is performed by the conventional acoustooptical element. For example, since tellurium dioxide, which has been generally used as the acoustooptical element, does not transmit the detection light having the wavelength of 300 nm or less, the acoustooptical element made of quartz, which has a sonic speed of 5960 m/sec being about ten times faster than comparing to tellurium dioxide, needs to be used. However, there is a problem that a focal length lengthens when the acoustooptical element made of quartz is used, because a focal length of a cylindrical lens effect by the acoustooptical element is inversely proportional to the wavelength of light output from the light source and proportional to a square of the sonic speed.

SUMMARY OF THE INVENTION

It is an object of the present invention to provide the optical reticle substrate inspection apparatus that can improve scanning stability when the laser light source having a short wavelength is used and the beam scanning method thereof.

An optical reticle substrate inspection apparatus according to the present invention comprises a laser, a first acoustooptical element which scans a laser beam output from said laser, a second acoustooptical element which generates a virtual image with a concave lens effect to said laser beam output from said first acoustooptical element, a concave lens arranged on the output side of said laser beam of said second acoustooptical element, and an optical system which images said virtual image on a reticle substrate being an object to be inspected. The concave lens magnifies said laser beam in a perpendicular direction to the scanning direction by said first acoustooptical element.

In the present invention, the first acoustooptical element performs laser beam scanning. Further, the second acoustooptical element generates a virtual image whose aberration is reduced to the laser beam, and the concave lens adjusts the shape of the virtual image in a circle, for example. Then, the optical system images the virtual image on the reticle substrate. As described, in the present invention, since not the convergence spot but the virtual image is imaged on the reticle substrate and its scanning is performed, stable scanning can be performed even if the laser beam having a short wavelength is used.

A beam scanning method of an optical reticle substrate inspection apparatus according to the present invention comprises the steps of generating a virtual image with an acoustooptical element to a laser beam, and imaging said virtual image on a reticle substrate being an object to be inspected.

BRIEF DESCRIPTION OF THE DRAWINGS

FIG. 2 is a schematic view showing a structure of an optical reticle substrate inspection apparatus according to a first embodiment of the present invention.

FIG. 3 is a schematic view showing a beam scanning method of the optical reticle substrate inspection apparatus according to the first embodiment of the present invention.

FIG. 4 is a schematic view showing a structure of an optical reticle substrate inspection apparatus according to a second embodiment of the present invention and its beam scanning method.

DETAILED DESCRIPTION OF THE PREFERRED EMBODIMENTS

Figure 1:
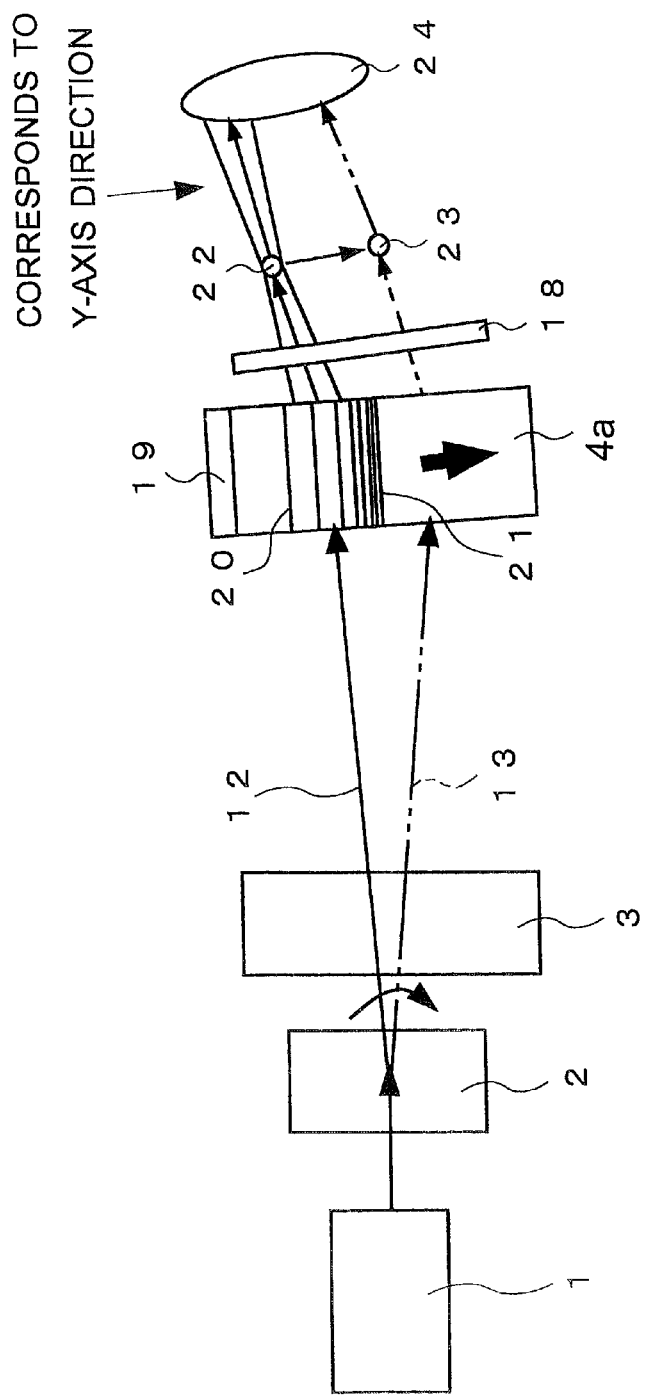
FIG. 1 is a schematic view showing a conventional optical reticle substrate inspection apparatus.

Preferred embodiments of the present invention will be specifically described with reference to the accompanying drawings as follows. FIG. 2 is a schematic view showing a structure of an optical reticle substrate inspection apparatus according to a first embodiment of the present invention.

In the optical reticle substrate inspection apparatus according to the first embodiment, similarly to the conventional apparatus, the laser light source 1, the acoustooptical element 2 and the group of cylindrical lenses 3 are arranged in this order in the rectilinear direction of the laser beam output from the laser light source 1. A laser wavelength of the laser light source 1 is 300 nm or less, for example. The acoustooptical element 2 is made of quartz, for example, and is arranged so as to scan the laser beam output from the laser light source 1 in a vertical direction to the straight line by the frequency modulation. The group of cylindrical lenses 3 is arranged so as to magnify the laser beam output form the acoustooptical element 2 only in the scanning direction by the acoustooptical element 2. Note that the scanning direction by the acoustooptical element 2 corresponds to the Y-axis direction.

In this embodiment, an acoustooptical element 4 showing the lens effect is further provided for the laser beam output from the group of cylindrical lenses 3. The transducer 19 is attached to one end portion of the acoustooptical element 4. The acoustooptical element 4 is arranged such that a side where the transducer 19 is attached, that is, a side where the ultrasonic is input, is closer to the group of cylindrical lenses 3. Furthermore, in this embodiment, a group of cylindrical concave lenses 5, which magnifies the laser beam output form the acoustooptical element 4 only in a perpendicular direction to the scanning direction and outputs it, is provided. A numerical aperture of the group of cylindrical concave lenses 5 equals a numerical aperture of the acoustooptical element 4 when it functions as the cylindrical concave lens. Therefore, the shape of the virtual image formed by the acoustooptical element 4 and the group of cylindrical concave lenses 5 is the circle.

Moreover, an optical system 8 is provided which images the laser beam output from the group of cylindrical concave lenses 5. A relay lens 7 which propagates the laser beam output from the group of cylindrical concave lenses 5 to the optical system 8 in the post-step is arranged between the group of cylindrical concave lenses 5 and the optical system 8. The optical system 8 has a structure same as that of a conventional system. For example, the optical system is provided with a group of lenses necessary for imaging, a measure for detecting fluctuation of the intensity and the like of the laser beam, a splitter necessary in a multi-beam inspection method, a detector for detecting a reticle substrate reflection light and the like. Further, an objective lens 9 that performs convergence close to a theoretical spot limit is arranged between the optical system 8 and a reticle substrate 10 being an object to be inspected. Furthermore, a detector 11 that detects the intensity and the like of the laser beam passed through the reticle substrate 10 is provided to the optical reticle substrate inspection apparatus. The acoustooptical element 2, the group of cylindrical lenses 3, the acoustooptical element 4 and the group of cylindrical concave lenses 5 may constitute a concave lens type scanning portion 6.

Note that a magnification of the group of cylindrical lenses 3 may be set so as to equal a distance between the forefront portion and the aftermost portion when a series of ultrasonic oscillated from the transducer 19 propagates the acoustooptical element 4, for example.

Next, description will be made for the beam scanning method of the optical reticle substrate inspection apparatus according to the first embodiment constituted as above. FIG. 3 is a schematic view showing a beam scanning method of the optical reticle substrate inspection apparatus according to the first embodiment of the present invention. FIG. 3 shows the laser light source 1 to the relay lens 7.

In this beam scanning method, scanning is performed in the angle made by the incident direction and the output direction to the laser beam output from the laser light source 1 by utilizing the frequency modulation by the acoustooptical element 2. At this point, a frequency band modulated by the acoustooptical element 2 for scanning in the angle can be arbitrarily decided based on a size of the virtual image formed by the acoustooptical element 4, a moving distance of the virtual image with scanning, and a spot size imaged on a surface of the reticle substrate 10. The optical path of the laser beam transits from the path 12 to the path 13 due to this scanning. When the laser beam has its optical path on the path 12, the laser beam is magnified by the group of cylindrical lenses 3 and output as the laser beam 30 with the width in the scanning direction.

Further, the transducer 19 outputs a series of ultrasonic which is swept such that the wavelength becomes shorter in linear state as the passage of time. A plurality of the parallel lines between an aftermost portion 25 and a forefront portion 26 in FIG. 3 show that the wider the distance between the lines the longer the wavelength. A distance between the forefront portion 26 and the aftermost portion 25 of a series of the ultrasonic equals the width of the laser beam 30. When the laser beam 30 is made incident to the acoustooptical element 4, diffraction of the laser beam 30 occurs by an ultrasonic pulse, in which the frequency is swept such that the wavelength becomes shorter in linear state from the forefront portion 26 to the aftermost portion 25 as described above. At this time, since the wavelength of the ultrasonic is different in accordance with a spatial position of the laser beam 30, Bragg angle is also different, and thus the concave lens effect occurs in this embodiment. Accordingly, the acoustooptical element 4 functions as the concave lens, and a circular virtual image 14 is formed on a side where the laser beam 30 is made incident by a combinational function with the group of cylindrical concave lenses 5. Further, when the laser beam has its optical path on the path 13, a circular virtual image 15 is formed at a position off from the virtual image 14 in the scanning direction.

The laser beam 30 output from the acoustooptical element 4 is made incident to the optical system 8 via the group of cylindrical concave lenses 5 and the relay lens 7 while magnifying its width. Then, the optical system 8 controls a traveling direction, an aperture and the like of the laser beam 30, and makes the virtual image 14 to be imaged as a spot 17 on the surface of the reticle substrate 10 via the objective lens 9. The spot 17 imaged on the surface of the reticle substrate 10 moves in the Y-axis direction with an angle scanning by the acoustooptical element 2, and when the laser beam output from the acoustooptical element 2 has its optical path on the path 13, the virtual image 15 is imaged on the surface of the reticle substrate 10 as a spot 16. Then, the intensity and the like of the transmission light are detected by the detector 11.

In such a scanning method, assuming that a propagation speed of ultrasonic in the acoustooptical element 4 is V (m/sec.), the wavelength of the laser beam is (m), a sweeping time of ultrasonic (output time of a series of ultrasonic) in the transducer 19 is T (sec.), and the band of ultrasonic oscillated from the transducer 19 is f (Hz), a focal length f (m) when the acoustooptical element 4 shows the cylindrical concave lens effect is expressed by the following expression 1.

$$f = \left| \frac{V^2 T}{\lambda \Delta f} \right| \qquad \text{[Expression 1]}$$

This expression 1 also shows that the focal length is inversely proportional to the wavelength of the incident laser and proportional to a square of the ultrasonic speed. Thus it is understood that the focal length lengthens when the acoustooptical element made of quartz is used, which has a fast ultrasonic propagation speed of 5960 (m/sec.), comparing to the acoustooptical element made of tellurium dioxide having the ultrasonic propagation speed of 620 (m/sec.) as in the foregoing.

Since this embodiment has a constitution where the acoustooptical element 4 is used so as to generate the concave lens effect and relay the virtual image, a total optical path length can be shortened comparing to the conventional beam scanning method using a cylindrical convex lens effect. Particularly in a current state, only the acoustooptical element made of quartz having a fast sonic speed (ultrasonic propagation speed) can be used in a laser wavelength shorter than 300 nm, a remarkable effect is exerted. For example, in the case where the propagation speed V is 5960 (m/sec.), the wavelength of the laser beam is 244×10$^{-9}$ (m), the sweeping time of ultrasonic (output time of a series of ultrasonic) T is 2×10$^{-6}$ (sec.), and the band of ultrasonic f is 80×10$^{-6}$ (Hz), the focal length f is 3.64 m according to the foregoing expression 1. Therefore, when the acoustooptical element is made to exert the convex lens effect to relay the convergence spot and scanning is performed conventionally, the optical path lengthens by a length corresponding to about 2×f, which is not realistic when the stability is considered. On the other hand, according to the present embodiment, since the acoustooptical element is used so as to function as the concave lens, the virtual image is relayed, and thus the optical path of a scanning optical system can be shortened. For this reason, the stable scanning can be performed even when the acoustooptical element made of quartz having a fast ultrasonic propagation speed is used.

Next, description will be made for a second embodiment of the present invention. In the first embodiment, the frequency is swept such that the wavelength of the ultrasonic pulse of the acoustooptical element 4 becomes shorter from the forefront portion 26 to the aftermost portion 25, but the sweeping direction of the frequency is reversed in the second embodiment. FIG. 4 is a schematic view showing a structure of an optical reticle substrate inspection apparatus according to the second embodiment of the present invention and its beam scanning method. Note that the same reference numerals are added to the same constituent elements as the first embodiment shown in FIG. 2 and FIG. 3, and their detail description will be omitted.

In the second embodiment, the acoustooptical element 4 is arranged such that a side where the transducer 19 is attached, that is, a side where ultrasonic is input is made far from the group of cylindrical lenses 3. Other part of the structure is the same as that of the first embodiment.

In the beam scanning method for the second embodiment constituted in this manner, the transducer 19 outputs a series of ultrasonic such that the wavelength lengthens in linear state as the passage of time. A plurality of parallel lines between the aftermost portion 27 and the forefront portion 28 in FIG. 4 show that the wider the distance between the lines the longer the wavelength. The distance between the forefront portion 28 and the aftermost portion 27 of the series of ultrasonic equals the width of the laser beam 30 similarly to the first embodiment. When the laser beam 30 is made incident to the acoustooptical element 4, diffraction of the laser beam 30 occurs due to the ultrasonic pulse, in which the frequency is swept such that the wavelength lengthens in linear state as described above. Thus, the concave lens effect occurs in this embodiment as well. Then, the circular virtual image 14 is formed on a side where the laser beam 30 is made incident by the combinational function with the group of cylindrical concave lenses 5. When the laser beam has its optical path on the path 13, the circular virtual image 15 is formed on a position off from the virtual image 14 in the scanning direction.

Therefore, an effect that the stable scanning can be performed is obtained by the second embodiment similarly to the first embodiment by performing the same scanning as the first embodiment.

What is claimed is:

1. A beam scanning method of an optical reticle substrate inspection apparatus, comprising the steps of:

scanning a laser beam output from a laser in a first scanning direction using a first acoustooptical element;

generating a virtual image with a second acoustooptical element using the laser beam output from the first acoustooptical element;

magnifying said laser beam output from the second acoustooptical element in a second direction; and imaging said virtual image on a reticle substrate being an object to be inspected.

2. The beam scanning method of the optical reticle substrate inspection apparatus according to claim 1, wherein a wavelength of said laser is 300 nm or less.

3. The beam scanning method of the optical reticle substrate inspection apparatus according to claim 1, wherein at least one of said acoustooptical elements is made of quartz.

4. The beam scanning method of the optical reticle substrate inspection apparatus according to claim 2, wherein at least one of said acoustooptical elements is made of quartz.

* * * * *